US010709676B2

(12) United States Patent
Pan et al.

(10) Patent No.: US 10,709,676 B2
(45) Date of Patent: Jul. 14, 2020

(54) APPLICATIONS OF SPERMINE AND DERIVATIVES THEREOF

(71) Applicant: GENEHEAL BIOTECHNOLOGY CO., LTD., Guangdong (CN)

(72) Inventors: Wuguang Pan, Guangdong (CN); Wei Zhu, Guangdong (CN)

(73) Assignee: Geneheal Biotechnology Co., Ltd., Guangzhou (CN)

( * ) Notice: Subject to any disclaimer, the term of this patent is extended or adjusted under 35 U.S.C. 154(b) by 0 days.

(21) Appl. No.: 16/334,273

(22) PCT Filed: Sep. 8, 2017

(86) PCT No.: PCT/CN2017/101059
§ 371 (c)(1),
(2) Date: Mar. 18, 2019

(87) PCT Pub. No.: WO2018/059211
PCT Pub. Date: Apr. 5, 2018

(65) Prior Publication Data
US 2019/0209493 A1    Jul. 11, 2019

(30) Foreign Application Priority Data
Sep. 29, 2016   (CN) .......................... 2016 1 0865149

(51) Int. Cl.
| | |
|---|---|
| *A61K 31/132* | (2006.01) |
| *C07C 209/00* | (2006.01) |
| *C07D 501/57* | (2006.01) |
| *A61P 3/00* | (2006.01) |
| *A61K 31/663* | (2006.01) |
| *A61K 38/17* | (2006.01) |
| *A61K 31/16* | (2006.01) |
| *A61K 38/06* | (2006.01) |
| *A61K 31/407* | (2006.01) |
| *A61P 25/14* | (2006.01) |
| *A61K 31/198* | (2006.01) |
| *C07F 9/90* | (2006.01) |
| *C07C 221/00* | (2006.01) |
| *A61P 43/00* | (2006.01) |
| *C07D 405/14* | (2006.01) |
| *A61K 31/427* | (2006.01) |
| *A61P 25/08* | (2006.01) |
| *C07C 249/00* | (2006.01) |
| *A61K 8/41* | (2006.01) |
| *A61K 31/00* | (2006.01) |
| *A61K 31/341* | (2006.01) |

(52) U.S. Cl.
CPC .............. *A61K 31/132* (2013.01); *A61K 8/41* (2013.01); *A61K 31/00* (2013.01); *A61K 31/16* (2013.01); *A61K 31/198* (2013.01); *A61K 31/341* (2013.01); *A61K 31/407* (2013.01); *A61K 31/427* (2013.01); *A61K 31/663* (2013.01); *A61K 38/06* (2013.01); *A61K 38/17* (2013.01); *A61P 3/00* (2018.01); *A61P 25/08* (2018.01); *A61P 25/14* (2018.01); *A61P 43/00* (2018.01); *C07C 209/00* (2013.01); *C07C 221/00* (2013.01); *C07C 249/00* (2013.01); *C07D 405/14* (2013.01); *C07D 501/57* (2013.01); *C07F 9/90* (2013.01)

(58) Field of Classification Search
CPC .................................................... A61K 31/132
USPC ........................................................ 514/551
See application file for complete search history.

(56) References Cited

U.S. PATENT DOCUMENTS

2004/0242701 A1   12/2004  Bilbeny Lojo et al.

FOREIGN PATENT DOCUMENTS

| CN | 1829496 | 9/2006 |
|---|---|---|
| WO | WO 2014/067038 | 5/2014 |

OTHER PUBLICATIONS

Jurecka et al., J. Inherit. Metab. Dis. (2015), V38, p. 231-242.*
Schafer et al. Drug Discovery Today, 2008, 13 (21/22), 913-916.*
Horig et al. Journal of Translational Medicine 2004, 2(44), p. 1-8.*
Mackenzie, Grahame et al., "Synthesis of Analogues of 5-Aminoimidazole Ribonucleotides and their Effects as Inhibitors and Substrates of the Enzymes, Phosphoribosylaminoimidazole Carboxylase and Phosphoribosylaminoimidazolesuccinocarboxamide Synthetase Involved in the Biosynthesis of Purine Nucleotides de novo". J.C. S. Chem. Comm, Jan. 1, 1976 (Jan. 1, 1976), vol. 12, pp. 453-455.
Chipperfield, J. R. et al., "Effects on the Activity of the Enzyme Phosphoribosyl-Aminoimidazole Carboxylase, Involved in the Biosynthesis of the natural substrate 5-Amino-1-β-D-Ribofuranosylimidazole-4-Carboxylic Acid 5'-Phosphate". Nucleosides and Nucleotides, Dec. 31, 1988 (Dec. 31, 1988), 7(5, 6), pp. 571-576.

(Continued)

*Primary Examiner* — Yong L Chu
(74) *Attorney, Agent, or Firm* — Fish & Richardson P.C.

(57) ABSTRACT

Provided are applications of spermine and derivatives thereof. On the basis of existing protein structure data and small molecule structure data, calculations and analysis are performed using software to screen and obtain compounds capable of effectively interfering with PAICS activity, reducing SAICAR synthesis, and ultimately reducing SAICAR accumulation, in order to achieve the goal of treating or reducing ADSL deficiency. A better effect in the treatment or improvement of ADSL deficiency is expected from the joint use of at least two of the described compounds.

13 Claims, 3 Drawing Sheets

(56) References Cited

OTHER PUBLICATIONS

Pegg, Anthony E., "The Function of Spermine". IUBMB Life. Jan. 6, 2014 (Jan. 6, 2014), No. 1, pp. 8-18.

Jaeken J, Van den Berghe G. (Nov. 10, 1984). "An infantile autistic syndrome characterized by the presence of succinylpurines in body fluids". *Lancet* 8411:1058-1061.

Spiegel, E.K., Colman, R.F., and Patterson, D. (Jul. 12, 2006). "Adenylosuccinatelyase deficiency". Mol Genet Metab 89, 19-31.

Clamadieu, C., Cottin, X., Rousselle, C., and Claris, O. (Feb. 2008). "Adenylosuccinatelyase deficiency: an unusual cause of neonatal seizure". Arch Pediatr 15, 135-138.

Castro, M., Perez-Cerda, C., Merinero, B., Garcia, M.J., Bemar, J., Gil Nagel, A., Torres, J., Bermudez. M., Garavito, P., Marie. S., et al. (Apr. 25, 2002). "Screening for adenylosuccinatelyase deficiency: clinical, biochemical and molecular findings in four patients". Neuropediatrics 33, 186-189.

Jurecka, A., Zikanova, M., Tylki-Szymanska, A., Krijt, J., Bogdanska, A., Gradowska, W., Mullerova, K., Sykut-Cegielska, J., Kmoch. S., and Pronicka, E. (Jun. 3, 2008). "Clinical, biochemical and molecular findings in seven Polish patients with adenylosuccinatelyase deficiency". Mol Genet Metab 94, 435-442.

Ciardo, F., Salerno.C., and Curatolo, P. (May 2001). "Neurologic aspects of adenylosuccinatelyase deficiency". J Child Neurol 16, 301-308.

Gitiaux, C., Ceballos-Picot. I., Marie. S., Valayannopoulos, V., Rio, M., Verrieres, S., Benoist. J.F., Vincent, M.F., Desguerre, I., and Bahi-Buisson, N. (2009). "Misleading behavioural phenotype with adenylosuccinatelyase deficiency". Eur J Hum Genet 17, 133-136. Published online Oct. 1, 2008.

Mierzewska. H., Schmidt-Sidor, B., Jurkiewicz, E., Bogdanska, A., Kusmierska. K., and Stepien, T. (Jan. 2009). "Severe encephalopathy with brain atrophy and hypomyelination due to adenylosuccinatelyase deficiency—MRI, clinical, biochemical and neuropathological findings of Polish patients". Folia Neuropathol 47. 314-320.

Van den Bergh F, Vincent MF. Jaeken J, Van den Berghe G. (Apr. 1, 1993). "Residual adenylosuccinase activities in fibroblasts of adenylosuccinase-deficient children: parallel deficiency with adenylosuccinate and succinyl-AICAR in profoundly retarded patients and non-parallel deficiency in a mildly retarded girl", J. Inherit. Metab. Dis. 16(2) 415-424.

*Pharmaceutical Salts: Properties, Selection and Use*, P Heinrich Stahl (Editor), Camille G. Wermuth (Editor), ISBN: 3-90639-026-8, Hardcover, 388 pages, Aug. 2002.

\* cited by examiner

APPLICATIONS OF SPERMINE AND DERIVATIVES THEREOF

CROSS-REFERENCE TO RELATED PATENT APPLICATIONS

This application is a U.S. National Phase Application under 35 U.S.C. § 371 of International Patent Application No. PCT/CN2017/101059, filed Sep. 8, 2017, and claims the priority of Chinese Application No. 201610865149.5, filed Sep. 29, 2016, which is incorporated by reference as if expressly set forth in its entirety herein.

FIELD OF THE INVENTION

The present disclosure relates to novel use of spermine and derivatives thereof.

BACKGROUND OF THE INVENTION

Anabolism of purine is a kind of prevalent and important biological metabolism in organisms. Its metabolic products, AMP and GMP, provide not only starting materials for biosynthesis of DNA and RNA in the organisms, but also purine bases which are necessary for synthesis of many key coenzymes (NAD, NADP, FAD and CoA), signal molecules (e.g., cAMP) and an important energy molecule ATP in the body. It is thus evident that the anabolism of purine lies in the core position of the whole metabolic network. Purine synthesis includes two synthetic pathways, i.e. de novo purine synthesis and salvage pathway.

Adenylosuccinatelyase deficiency (ADSL deficiency) is one metabolic disease which has deletion or disorder in de novo adenine synthesis and purine nucleotide metabolic pathway. This disease is primarily caused by the mutation or deletion of adenylosuccinatelyase in the patients, which results in the substrate SAICAR of this enzyme is unduly accumulated in cells and cannot be eliminated in time [Jaeken J, Van den Berghe G. (1984). An infantile autistic syndrome characterized by the presence of succinylpurines in body fluids. *Lancet* 8411:1058-1061.]. In 1984, Jaeken and Van den Berghe first detected the accumulation of this metabolite in body fluids of several patients with bradykinesia and autism. The patients with adenylosuccinatelyase deficiency usually develop symptoms such as severe dysplasia, bradykinesia, dull-looking, epilepsy, autism and the like [Spiegel, E. K., Colman, R. F., and Patterson, D. (2006). Adenylosuccinatelyase deficiency. Mol Genet Metab 89, 19-31. Clamadieu, C., Cottin, X., Rousselle, C., and Claris, O. (2008). Adenylosuccinatelyase deficiency: an unusual cause of neonatal seizure. Arch Pediatr 15, 135-138. Castro, M., Perez-Cerda, C., Merinero, B., Garcia, M. J., Bemar, J., Gil Nagel, A., Torres, J., Bermudez. M., Garavito, P., Marie. S., et al. (2002). Screening for adenylosuccinatelyase deficiency: clinical, biochemical and molecular findings in four patients. Neuropediatrics 33, 186-189. Jurecka, A., Zikanova, M., Tylki-Szymanska, A., Krijt, J., Bogdanska, A., Gradowska, W., Mullerova, K., Sykut-Cegielska, J., Kmoch. S., and Pronicka, E. (2008b). Clinical, biochemical and molecular findings in seven Polish patients with adenylosuccinatelyase deficiency. Mol Genet Metab 94, 435-442.].

ADSL deficiency has 3 types of continuous main phenotypes: neonatal lethal type, severe (type I) and mild-to-moderate (type II). It was clinically found that patients can have different phenotypes even they are from the same family. The oneset of the disease is generally from birth to infancy. The reported cases include lethal neonatal encephalopathy (manifested as hypokinesia, intractable epilepsy, respiratory disturbance), and moderate mental deficiency. All the patients have mental deficiency, and most of the patients have different types of epilepsy, and about one third of the patients have autism characteristics (unable to make eye contact, sensitive to sound and light, repetitive behaviors, agitation, temper tantrum, self-injury and self-mutilation). Other unusual clinical manifestations include psychomotor delay, overactivity, language disorder, hypotonia, muscular atrophy and spasm. Patients with severe ADSL deficiency usually have microcephaly. It has been reported that prenatal clinical manifestations include intrauterine growth retardation, microcephaly, fetal hypokinesia and absent of fetal heart rate variability.

In the metabolic pathway of adenine de novo synthesis, adenylosuccinatelyase (hereinafter referred to as ADSL enzyme) mainly participates in the catalytic cracking of SAICAR to form AICAR and in the reaction for generating AMP from S-AMP [Spiegel, E. K., Colman. R. F. and Patterson, D. (2006). Adenylosuccinatelyase deficiency. Mol Genet Metab 89, 19-31. Clamadieu. C., Cottin, X., Rousselle. C., and Claris. O. (2008). Adenylosuccinatelyase deficiency: an unusual cause of neonatal seizure. Arch Pediatr 15, 135-138. Castro. M., Perez-Cerda, C., Merinero, B., Garcia. M. J., Bemar. J., Gil Nagel, A., Torres. J., Bermudez. M., Garavito. P., Marie. S., et al. (2002). Screening for adenylosuccinatelyase deficiency: clinical. biochemical and molecular findings in four patients, Neuropediatrics 33, 186-189.]. In the patients with adenylosuccinatelyase deficiency, the harmful metabolite SAICAR cannot be eliminated in time due to the mutation or deletion of the ADSL enzyme, which usually makes the patients develop severe neurological and physiological symptoms, such as epilepsy, encephalodysplasia, bradykinesia and the like [Ciardo, F., Salerno. C., and Curatolo, P. (2001). Neurologic aspects of adenylosuccinatelyase deficiency. J Child Neurol 16, 301-308. Gitiaux, C., Ceballos-Picot. I., Marie. S., Valayannopoulos, V., Rio, M., Verrieres, S., Benoist. J. F., Vincent, M. F., Desguerre, I., and Bahi-Buisson, N. (2009). Misleading behavioural phenotype with adenylosuccinatelyase deficiency. Eur J Hum Genet 17, 133-136. Mierzewska. H., Schmidt-Sidor, B., Jurkiewicz, E., Bogdanska, A., Kusmierska. K., and Stepien, T. (2009). Severe encephalopathy with brain atrophy and hypomyelination due to adenylosuccinatelyase deficiency—MRI, clinical, biochemical and neuropathological findings of Polish patients. Folia Neuropathol 47. 314-320.]. A large amount of intermediate metabolites SAICAr, which is a product of the dephosphorylation of SAICAR, and S-Ado, which is a product of the dephosphorylation of S-AMP, are usually accumulated in the cerebrospinal fluid and body fluid of the patients [Spiegel, E. K., Colman, R. F., and Patterson, D. (2006). Adenylosuccinatelyase deficiency. Mol Genet Metab 89, 19-31. Mierzewska, H., Schmidt-Sidor, B., Jurkiewicz, E., Bogdanska, A., Kusmierska. K., and Stepien, T. (2009). Severe encephalopathy with brain atrophy and hypomyelination due to adenylosuccinatelyase deficiency—MRI, clinical, biochemical and neuropathological findings of Polish patients. Folia Neuropathol 47, 314-320.]. Van den Berghe et al. found that the ratio of S-do to SAICAr in the body fluid has certain correlation with the disease severity of the patient [Van den Bergh F, Vincent M F. Jaeken J, Van den Berghe G. (1993). Residual adenylosuccinase activities in fibroblasts of adenylosuccinase-deficient children: parallel deficiency with adenylosuccinate and succinyl-AICAR in profoundly retarded patients and non-parallel deficiency in a mildly retarded girl, J. Inherit. Metab. Dis. 16(2) 415-424.]. Until now, there is no clinically effective therapeutic regimens which can cure ADSL deficiency.

Phosphoribosylaminoimidazolesuccinocarboxamide synthetase/phosphoribosylaminoimidazole carboxylase, i.e. PAICS, is an important bifunctional enzyme in the purine de novo synthetic pathway. It has functions of SAICAR synthetase (4-(N-succinylcarboxamide)-5-aminoimidazole ribonucleotide synthetase, SAICARs) and AIR carboxylase (5-aminoimidazole ribonucleotide carboxylase, AIRc), and can catalyze the sixth and seventh steps of the reaction of purine de novo anabolism, in which one key reaction process is shown as follows

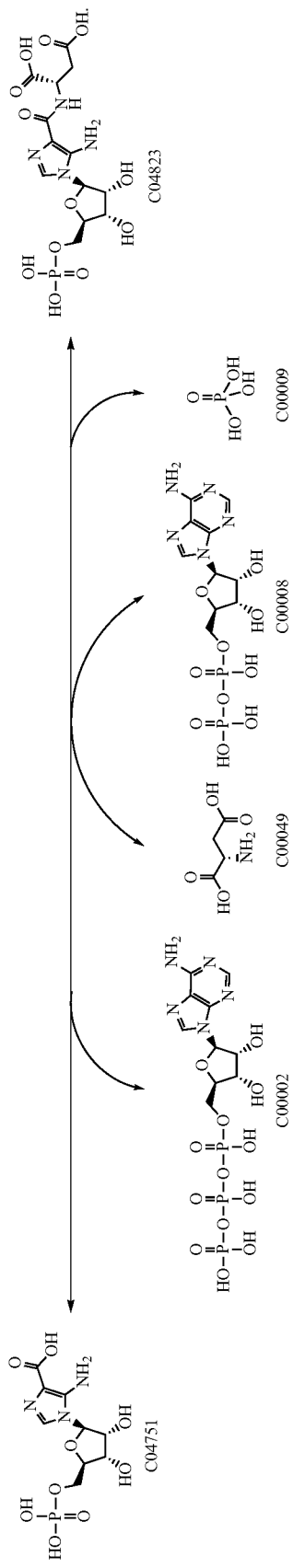

Preceding researches of the inventors show that the accumulation of SAICAR and SAICAr can be effectively reduced by interfering with the function of PAICS protein (gene), thereby achieving the goal of treating or improving ADSL deficiency. However, no compound has been reported to have such effect at present.

Spermine

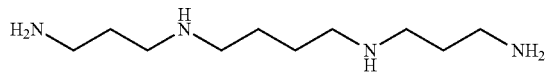 [SMILES: NCCCNCCCCNCCCN]

is a kind of polyamine substances which contains two amino groups and two imino groups. Spermine is obtained from putrescine (butanediamine) and S-adenosyl methionine through catalysis with various enzymes in organisms. Both spermine and spermidine are present in bacteria and most animal cells, and are important substances for promoting cell proliferation. Under acidic condition, it exhibits the characteristics of polycation polyamines and can bind with DNA molecules in viruses and bacteria to make the DNA molecules more stable and flexible. In addition, it is also one of necessary components in cell culture media. Therefore, spermine has been used as a nutritional supplement.

SUMMARY OF THE INVENTION

An objective of the present disclosure is to provide novel use of spermine and derivatives thereof.

The inventor, on the basis of existing data relating to the protein and small molecule structures, performs calculation and analysis using software, and find that a compound (spermine) with DrugBank ID DB00127 can effectively interfere with PAICS activity, then reduce SAICAR synthesis, and ultimately reduce SAICAr accumulation, thereby achieving the goal of treating or improving ADSL deficiency.

The pharmaceutically acceptable derivatives of the above compound may have the same parent core structure as the compound per se, and can produce molecules having the same or similar activity as the original compound through reactions such as hydrolysis and the like in vivo, resulting in the same or similar therapeutic efficacy.

The pharmaceutically acceptable derivatives of the compound may particularly refer to simple derivatives thereof, and especially refer to one of lower ester, lower ether, lower alkyl substituent, pharmaceutical salt, and lower amide thereof, i.e., derivatives obtained by condensation of carboxylic acid, alcohol, amine having 1 to 6, preferably 2 to 6, or 2 to 4 carbon atoms with the parent compound.

The pharmaceutically acceptable pharmaceutical salts of the compound can be synthesized from the parent compound by conventional chemical methods, such as the method described in *Pharmaceutical Salts: Properties, Selection and Use*, P Heinrich Stahl (Editor), Camille G. Wermuth (Editor), ISBN: 3-90639-026-8, Hardcover, 388 pages, August 2002. In general, such salts can be prepared by reacting free alkali of the compound with an acid in water, organic solvent or a mixed solution of both; generally, a non-aqueous media can be used, such as ethyl ether, ethyl acetate, ethanol, isopropanol or acetonitrile.

Acid addition salt may be prepared with various acids (inorganic acids and organic acids). The examples of the acid addition salt may include salts prepared from an acid which may be selected from a group consisting of acetic acid, 2,2-dichloroacetic acid, adipic acid, alginic acid, ascorbic acid (such as L-ascorbic acid), L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid (such as D-glucuronic acid), glutamic acid (such as L-glutamic acid), α-ketoglutaric acid, glycolic acid, hippuric acid, hydrobromic acid, hydrochloric acid, hydroiodic acid, hydroxyethylsulfonic acid, (+)-L-lactic acid, (+)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid and pentanoic acid, as well as acyl-amino acid and cation exchange resin.

By combined utilization of at least two of the above compounds, it is expected to obtain better effect of treating or improving ADSL deficiency.

BRIEF DESCRIPTION OF THE DRAWINGS

FIG. 3 shows the alignment result of different types of SAICAR synthetase protein sequences.

DETAILED DESCRIPTION OF THE EMBODIMENTS

Figure 1:
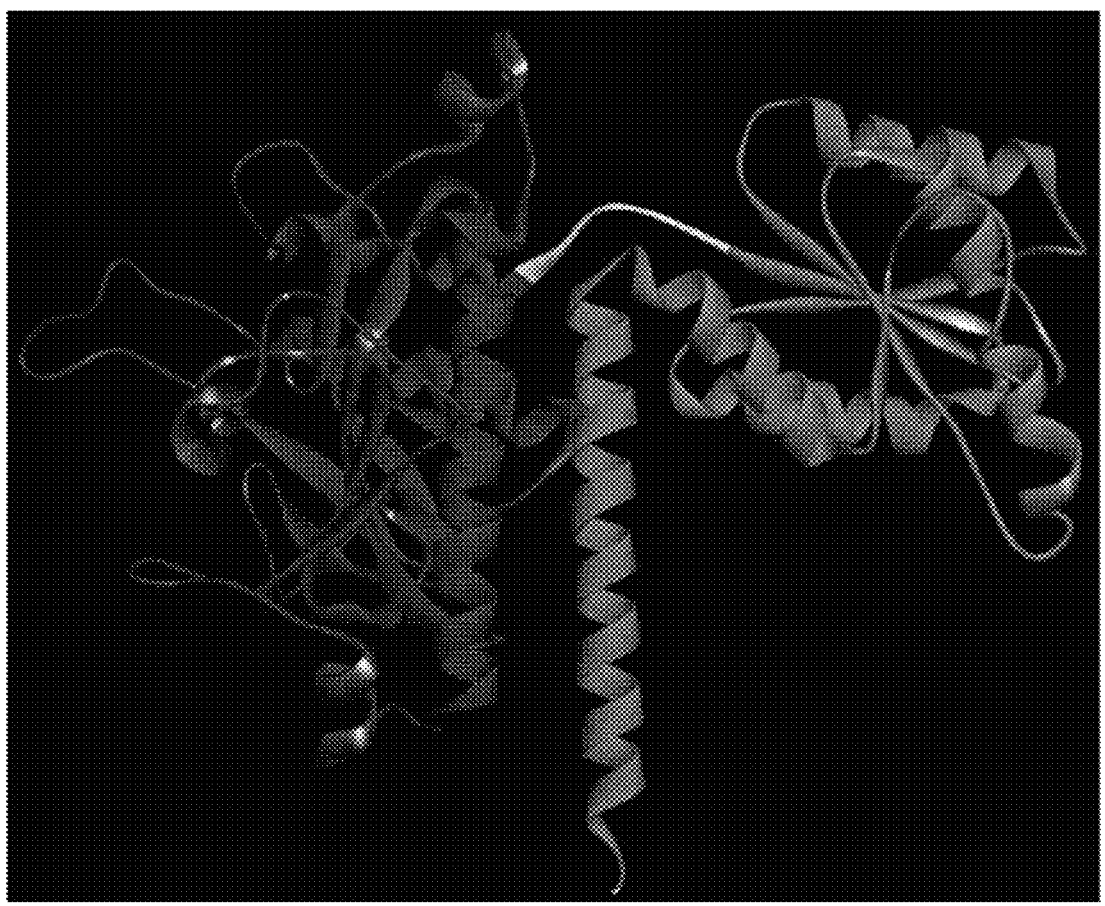
FIG. 1 shows a 3D solid ribbon structure diagram of PAICS.

There are 425 amino acid residues in full length of the human PAICS protein sequence, in which a fragment of 2-260 AA is a SAICAR synthetase domain, and a fragment of 267-425AA is an AIR carboxylase domain, these two domains are linked by a 6-peptide (KSESQC). Furthermore, GLN159-GLN183 α-helix in the SAICAR synthetase domain and ASN395-ASN424 α-helix in the AIR carboxylase domain interact with each other and tightly bind together, as shown in FIG. 1.

A protein structure data bank (RCSB) collects the crystal structure data of SAICAR synthetases of different origins, which includes *Saccharomyces cerevisiae* (1A48, 2CNQ, 2CNV, 2CNU, 1OBD, 1OBG), *Pyrococcus horikoshii* OT3 (3U54, 3U55), *Escherichia coli* (2GQR, 2GQS), *Methanocaldococcus jannaschii* (2YZL, 2Z02), *Streptococcus pneumonia* (4FGR, 4FE2), *Mycobacterium abscessus* ATCC 19977/DSM 44196 (3R9R), *Thermotoga maritime* (1KUT), *Clostridium perfringens* (3NUA), *Ehrlichia chaffeensis* (3KRE), *Geobacillus kaustophilus* (2YWV) as well as PAICS crystal structure data of *Homo sapiens* (2H31) and *Bombyx mori* (4JAO). Wherein, there are complexes 2GQS, 2CNQ and 4FE2 which contain the structure of CAIR, and complexes 2CNV, 2CNU and 4FE2 which contain the structure of ASP.

Figure 2:
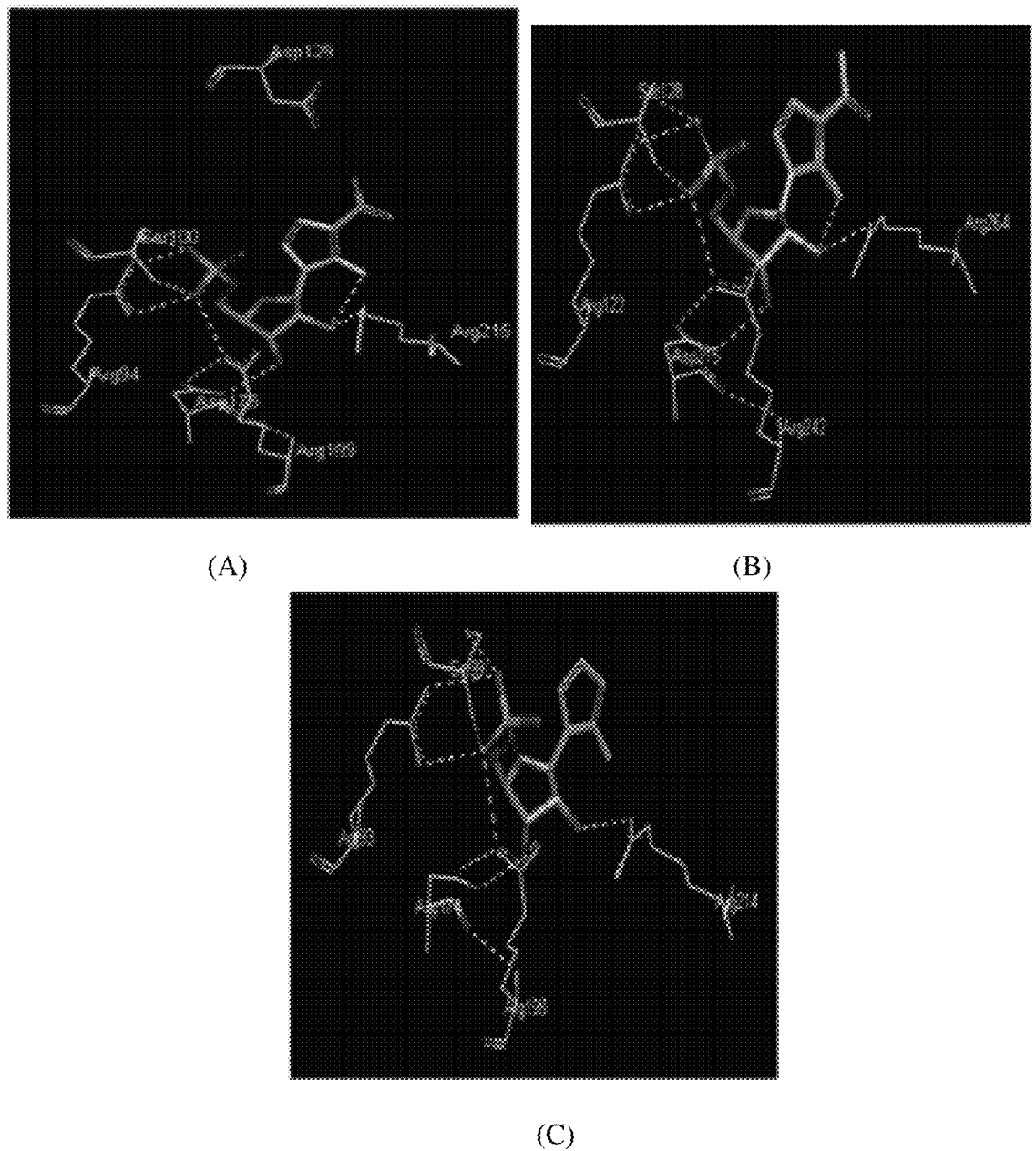
FIG. 2 shows diagrams indicating the interaction of CAIR and SAICAR synthetase in the crystal structure, in which A: PDB access ID 2GQS; B: PDB access ID 2CNQ; and C: PDB access ID 4FE2.
Figure 3:
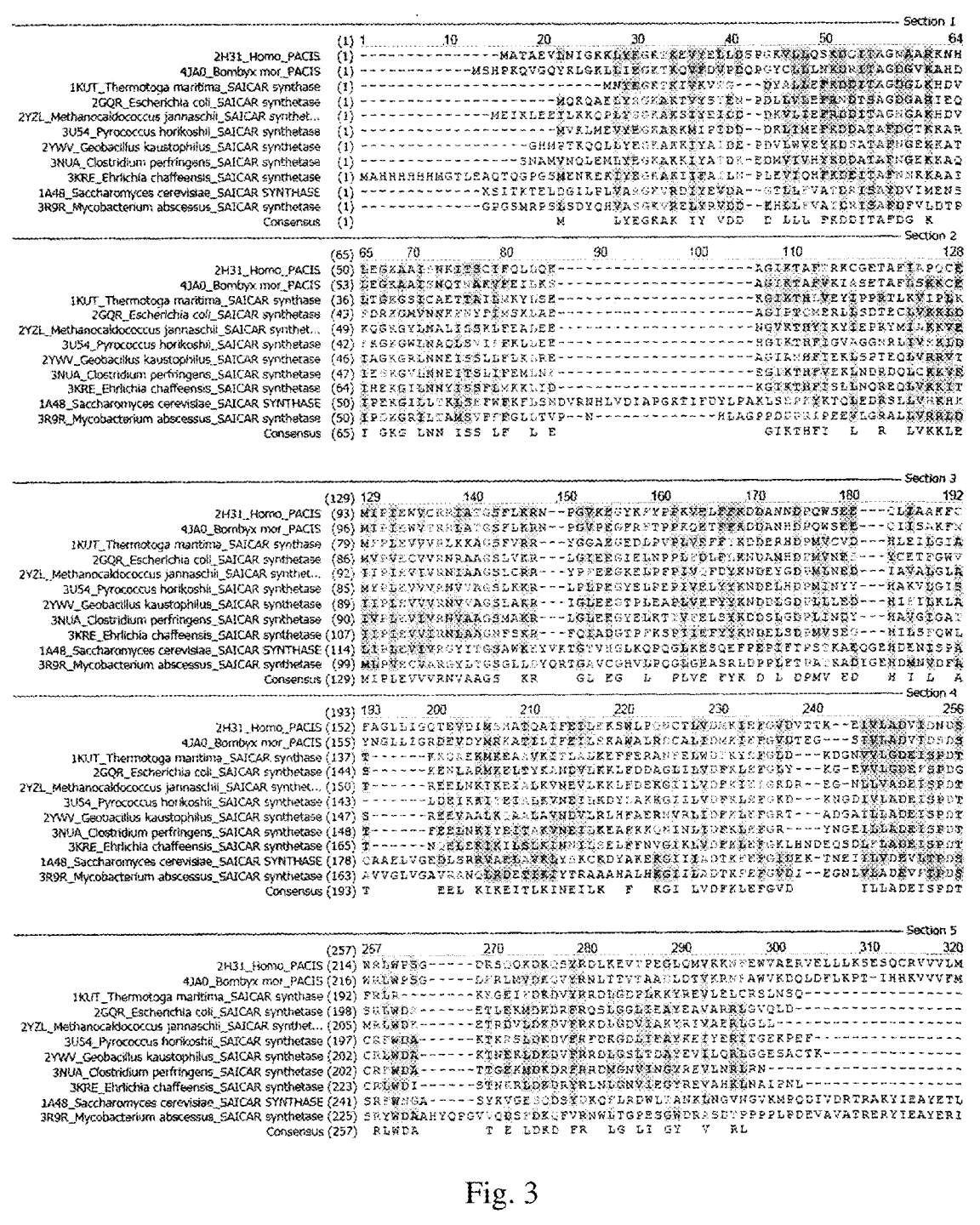

As shown in FIG. 2, the residues within CAIR 3 Å in 2CNQ are Arg122, Ser128, ASP215, Arg242 and Arg264; the residues within CAIR 3 Å in 2GQS are Arg94, Ser100, ASP129, ASP175, Arg199 and Arg215; the residues within CAIR 3 Å in 4FE2 are Arg93, Ser99, ASP174, Arg199, and Arg214. With reference to the alignment result of the SAICAR protein sequences of different species (FIG. 3), it can be seen that the binding sequences of SAICAR synthetases of different species with CAIR exhibits high-level conservative, and CAIR is primarily fixed by hydrogen bonds.

On the basis of the above results, the crystal structure conformations in SAICAR synthetases of *Saccharormyces cerevisiae* (PDB: 2CNQ) and *Escherichia coli* (PDB: 2GQS) are used as receptor structures for calculating and screening, since there is no conformation which can bind CAIR in human PAICS crystal structure, and no catalytic conformation formed in the catalytic region, and the results obtained by calculation are not reliable. 4661 of small molecule drugs in the DrugBank (http://www.drugbank.ca/downloads#structures) are calculated and screened by using the ligand fit module of Discovery studio. The calculating results show that DB00127 (common name: Spermine) has a Dock Score of 316.723, indicating that the compound spermine can effectively interact with PAICS, influence SAICAR synthesis. Thus, it is expected that this compound can be developed as a drug for treating ADSL deficiency or health-care product for improving the ADSL deficiency.

Further, it is confirmed by biochemical enzyme activity experiments and cell biology experiments that the inhibition ratio of the compound spermine against SAICAR accumulation can reach 71.1%. By inhibiting the activity of PAICS, the accumulation of toxic compound SAICAR is reduced, which proves that the compound spermine can effectively treat rare disease ADSL deficiency.

The pharmaceutically acceptable derivatives of the above compound has the same parent core structures as the compound per se, and can produce molecules having the same or similar activity as the original compound through reactions such as hydrolysis and the like in vivo, resulting in the same or similar therapeutic efficacy.

The pharmaceutically acceptable derivatives of the compound may particularly refer to simple derivatives thereof, and especially refer to one of lower ester, lower ether, lower alkyl substituent, pharmaceutical salt and lower amide thereof, i.e., derivatives obtained by condensation of carboxylic acid, alcohol, amine having 1 to 6, preferably 2 to 6, or 2 to 4 carbon atom(s) with the parent compound.

The pharmaceutically acceptable pharmaceutical salts of the compound can be synthesized from the parent compound by conventional chemical methods, such as the method described in *Pharmaceutical Salts: Properties, Selection and Use*, P Heinrich Stahl (Editor), Camille G. Wermuth (Editor), ISBN: 3-90639-026-8, Hardcover, 388 pages, August 2002. In general, such salts can be prepared by reacting free alkali of the compound with an acid in water, organic solvent or a mixed solution of both; generally, a non-aqueous media can be used, such as ethyl ether, ethyl acetate, ethanol, isopropanol or acetonitrile.

Acid addition salts can be prepared with various acids (inorganic acids and organic acids). The examples of the acid addition salts may includes salts prepared from an acid which may be selected from a group consisting of acetic acid, 2,2-dichloroacetic acid, adipic acid, alginic acid, ascorbic acid (such as L-ascorbic acid), L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid (such as D-glucuronic acid), glutamic acid (such as L-glutamic acid), α-ketoglutaric acid, glycolic acid, hippuric acid, hydrobromic acid, hydrochloric acid, hydroiodic acid, hydroxyethylsulfonic acid, (+)-L-lactic acid, (±)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid and pentanoic acid, as well as acyl-amino acid and cation exchange resin.

Combined utilization of the drugs can improve therapeutic effect, and reduce toxic and side effects to a certain extent. Preferably, 2, 3, 4, 5 or more compounds or derivatives thereof can be simultaneously used as the active ingredients for treating ADSL deficiency.

What is claimed is:

1. A method for treating or alleviating a disease comprising:
    administering a therapeutically effective amount of a compound or a pharmaceutically acceptable salt or $C_1$-$C_6$ amide thereof to a patient in need thereof,
    wherein the compound is spermine and the disease is ADSL deficiency.

2. The method according to claim 1, wherein the method comprises administering spermine to the patient.

3. The method according to claim 1, wherein the method comprises administering a pharmaceutically acceptable salt of spermine to the patient.

4. The method according to claim 3, wherein the pharmaceutically acceptable salt is prepared from spermine and an acid selected from the group consisting of acetic acid, 2,2-dichloroacetic acid, adipic acid, alginic acid, ascorbic acid, L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid, glutamic acid, α-ketoglutaric acid, glycolic acid, hippuric acid, hydrobromic acid, hydrochloric acid, hydroiodic acid, hydroxyethylsulfonic acid, (+)-L-lactic acid, (+)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acyl-amino acid.

5. The method of claim 1, wherein the ADSL deficiency is neonatal lethal type ADSL deficiency, type I ADSL deficiency, or type II ADSL deficiency.

6. The method of claim 4, wherein the pharmaceutically acceptable salt is prepared from spermine and hydrochloric acid.

7. The method of claim 4, wherein the pharmaceutically acceptable salt is prepared from spermine and sulfuric acid.

8. The method of claim 4, wherein the pharmaceutically acceptable salt is prepared from spermine and phosphoric acid.

9. The method of claim 4, wherein the pharmaceutically acceptable salt is prepared from spermine and acetic acid.

10. The method of claim 4, wherein the pharmaceutically acceptable salt is prepared from spermine and maleic acid.

11. The method of claim 4, wherein the pharmaceutically acceptable salt is prepared from spermine and nitric acid.

12. The method of claim 4, wherein the pharmaceutically acceptable salt is prepared from spermine and citric acid.

13. The method of claim 4, wherein the pharmaceutically acceptable salt is prepared from spermine and methanesulfonic acid.

* * * * *